June 23, 1964 A. H. V. BLOOM Plant Pat. 2,414
RUDBECKIA PURPUREA (ECHINACEA PURPUREA) PLANT
Filed Jan. 30, 1963
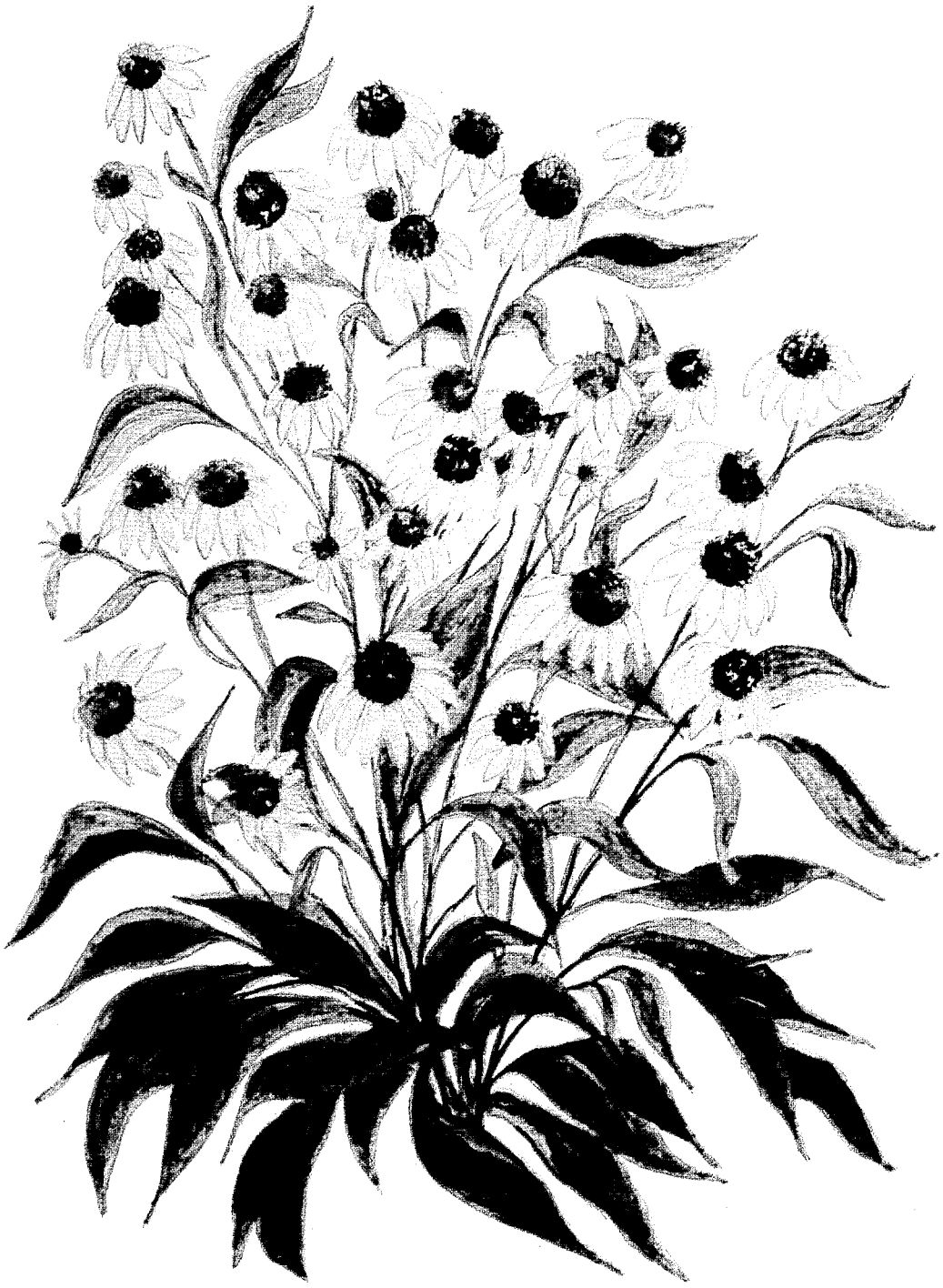
INVENTOR,
Alan H. V. Bloom,
by:- John H. Leonard,
his ATTY.

United States Patent Office

Plant Pat. 2,414
Patented June 23, 1964

2,414
*RUDBECKIA PURPUREA (ECHINACEA PURPUREA)* PLANT

Alan H. V. Bloom, Norfolk, England, assignor to The Wayside Gardens Company, Inc., Mentor, Ohio, a corporation of Ohio Filed Jan. 30, 1963, Ser. No. 255,138
1 Claim. (Cl. Plt.—68)

This invention relates to a new variety of *Rudbeckia,* or *Echinacea, purpurea* plant.

The present plant is a seedling, selected from a large number of seedlings which, in turn, arose from previous reselections covering several generations. The original seed of this strain were from a *Rudbeckia purpurea* known as "The King" and a *Rudbeckia purpurea* known as "Abendsonne" (both unpatented).

The new variety was asexually reproduced by me at Bressingham, England, by division and root cuttings.

The drawing shows in color, a number of stalks with leaves and blooms, from which some of the leaves have been omitted so to disclose the more prolific blooming, free branching, and compactness of the plant.

The roots are a fibrous mass ranging in depth from shallow to medium, with good resistance to drought and wetness.

The exposed plant is hardy, herbaceous, and of generally bushy growth with a rounded top. It is more upright and bushy than The King. A three year old plant is from 2½ to 3 feet high and about 18 inches to 30 inches in width. It is symmetrical and bushier than other varieties or species of Rudbeckia. It ranges from medium to vigorous in growth.

The exposed portion of the plant has exceptional resistance to low temperature, both when protected and unprotected.

For growth it prefers intense sun or partial shade with a southeast or west exposure. It prefers well drained sandy loam, but grows well in normal to wet, light to heavy, soils of all types.

The main stalks of the plant grow upright and are much more branched than usual. For this type of plant, they are otherwise usual and adequate to support the foliage and blooms well.

Both old and new growth are of the usual uniform color.

The main stalks range from two feet to three feet in length. They have the usual surface texture and manner of growth from the roots, with rough pubescent or usual upper faces.

The branches are alternate, and usual.

The foliage in general is compact, more so than shown in the drawing and than is general for Rudbeckia plants. The leaves are alternate in arrangement and abundant in quantity.

The color of both old leaves and new leaves, on both top and bottom, is the usual green and is uniform. The leaves are of the usual size and shape and of medium thickness.

The petioles or leaf stems are strong and of the usual color, length and surface texture.

The plant grows and blooms well in temperate regions such as are found in the continental United States, and particularly the Central and Northeast to Southern United States. It prefers sun but does well in light shade. It prefers eastern, southern and western exposures and responds only from fairly to poorly in northern exposures. It prefers moist, cool seasons, and well drained soil, whether acid, alkaline or neutral, but it grows well in moist soil, if the soil is not too damp. It prefers rich, sandy loom.

The quality of the blooms decreases with too much shade or too wet seasons or locations, but the quality is not reduced appreciably by dry conditions. The same is true as to quantity except, that shady locations reduce quantity.

The color and size of blooms are not affected appreciably by these different conditions.

The plant blooms from late June until frost, the blooming being continuous for this period. Cutting of part of the flowers appears not to change the blooming characteristics or period.

The references hereinafter made to color charts are to the Horticultural Color Chart of the British Royal Horticultural Society.

The buds are of the usual size and shape, have the usual aspect, and are borne in the usual manner. The petal color, when the sepals first divide is Erythrite Red, Chart 0027/3, with shadings of Magenta Rose, Chart 027. When half blown, the color ranges from Magenta Rose, Chart 027, to Garnet Lake, Chart 828/1, with undertones of Peony Purple, Chart 729.

The sepals and calyx are of the usual shape, size and surface texture.

The peduncles average from 18 inches to 36 inches in length, and have the usual surface texture, color, and strength.

The pedicels, branching from the peduncles, average from 8 to 24 inches in length. They have the usual texture, color and strength.

The blooms average from 4 to 6 inches in diameter, and an average plant will bear from 30 to 60 blooms. The blooms are borne singly. On the plant, they last several weeks, and when cut, they remain in good to excellent condition for 5 to 10 days. Each bloom has about 20 to 24 petals.

The petalage generally ranges in color from Magenta Rose, Chart 027, to Garnet Lake, Chart 828/1, with undertones of Peony Purple, Chart 729. The color is uniform throughout the extent of the petals, except that the reverse is slightly lighter, with a slight green tint toward the tip.

The center of the flower is generally cone shaped, and approximately 2 inches across and 1½ inches to 2 inches high.

The general tonality of the plant from a distance, when it is in bloom, is the same as that of the petals. The color fades as the flowers are spent and the seed develop in the center cone. Generally the color fades very gradually over two to three weeks or longer to Erythrite Red, Chart 0027/3.

The petals are usual in shape, texture, and arrangement except that they are somewhat wider than those of other types. The persistence of the petals is good both for cut and uncut blooms. The flower is a true single flower.

The blooms have the usual fragrance. Its lasting quality, both in cut and uncut flowers, is good.

The stamens, styles, stigmas, ovaries, and pollen are of the usual shape, color, and quantity for plants of this type.

The drawing further illustrates the characteristics of the variety and the following tabulation is a detailed description of the new variety:

*General*

Parentage: Selected seedling from several generations, starting with original seed from *Rudbeckia purpurea,* known as "The King" and Rudbeckia known as "Abendsonne."

Classification: Botanic.—*Rudbeckia purpurea,* also known as *Echinacea purpurea.*

*Flower*

Blooming habit:
*Location where observations were made.*—Bressingham, Norfolk, England and Mentor, Ohio.
Flowering.—Continuous from late June to frost.

Bud:
*Size.*—Usual.
*Form.*—Usual.
*Color.*—When sepals first divided, petals are Erythrite Red, Chart 0027/3, with shadings of Magenta Rose, Chart 027; when petals begin to unfurl, the color is the same as above. When half blown, the color ranges from Magenta Rose, Chart 027 to Garnet Lake, Chart 828/1 with undertones of Peony Purple, Chart 729.
*Sepals.*—Usual.
*Calyx.*—Shape, size and surface texture, usual.
*Peduncle.*—Length, average 18 to 36 inches. Aspect, color and strength, usual.
*Openings.*—Usual.

Bloom:
*Size.*—Average 4 to 6 inches in diameter.
*Borne.*—Singly.
*Stems.*—Length, 8 to 24 inches, branching from peduncle, strong. Aspect, color and strength usual.
*Form.*—Usual.
*Permanence.*—On the plant, lasts several weeks. When cut, good to excellent, 5 to 10 days.

Petalage:
*Number of petals under normal conditions.*—20 to 24.
*Colors.*—Inside ranging from Magenta Rose, Chart 027 to Garnet Lake, Chart 828/1 with undertones of Peony Purple, Chart 729.
*Variegations.*—The color is uniform throughout except slightly lighter with greenish tinge toward tips on reverse of petals.
*Discoloration.*—Fades very gradually with age, turning more toward Erythrite Red, Chart 0027/3 over a period of two to three weeks or longer.

Petals:
*Texture.*—Usual.
*Appearance.*—Usual, except somewhat wider than normal.
*Form.*—Usual.
*Arrangement.*—Usual.
*Persistence.*—Good.

Petals:
*Fragrance.*—Usual.
*Lasting quality.*—Usual.

Genital organs:
*Stamens.*—Usual.
*Color.*—Usual.
*Arrangement.*—Usual.
*Color.*—Usual.
*Pollen.*—Usual.
*Styles.*—Usual.
*Stigmas.*—Usual.
*Ovaries.*—Usual.

*Plant*

Form: Symmetrical and bushy with rounded top and generally upright growth.
Growth: Vigorous.
Foliage: Dense with alternate ararngements.
*Size.*—Usual.
*Quantity.*—Usual.
*Color.*—Usual.
*Shape.*—Usual with medium thickness.
*Texture.*—Both surfaces rough and pubescent or usual.
*Edge.*—Usual.
Petiole: Length, color and surface texture, usual. Strong.
Wood: New wood.—usual. Old wood.—usual.

The most distinctive feautres and characteristics of the new *Rudbeckia,* or *Echinacea, purpurea* plant are the compact, free branching, and upright growth as a result of which the plant, as a whole, stands up better than previous varieties providing a more colorful and shapely display; its much more prolific blooming than other known varieties; its free branching which produces a more compact plant than those previously known; the characteristics that each branch produces a flower whereby more blooms are provided and are better situated on the plant; and flower color which is richer and flower size which is larger and more uniform than in the case of other known varieties.

Having shown and described my new variety *Rudbeckia,* or *Echinacea, purpurea* plant, and its manner of asexual reproduction, I claim:

The new and distinct variety of *Rudbeckia* (*Echinacea*) *purpurea* plant, as herein shown and described.

No references cited.